(12) United States Patent
Pnita et al.

(10) Patent No.: US 9,994,606 B2
(45) Date of Patent: Jun. 12, 2018

(54) PROCESS FOR THE PURIFICATION OF REBAUDIOSIDE A AND COMPOSITIONS THEREOF

(71) Applicant: Almendra Pte Ltd., Singapore (SG)

(72) Inventors: Chutasmit Pnita, Bangkok (TH); Porntape Makarukpinyo, Bangkok (TH); Jamaluddin Bin Haja Mohideen, Chonburi (TH)

(73) Assignee: ALMENDRA PTE LTD., Singapore (SG)

( * ) Notice: Subject to any disclaimer, the term of this patent is extended or adjusted under 35 U.S.C. 154(b) by 335 days.

(21) Appl. No.: 13/709,562

(22) Filed: Dec. 10, 2012

(65) Prior Publication Data

US 2013/0164434 A1 Jun. 27, 2013

Related U.S. Application Data

(60) Provisional application No. 61/576,430, filed on Dec. 16, 2011.

(51) Int. Cl.

| | |
|---|---|
| *A23L 1/22* | (2006.01) |
| *B01J 19/10* | (2006.01) |
| *C07H 15/256* | (2006.01) |
| *C07H 15/24* | (2006.01) |
| *A23L 1/236* | (2006.01) |
| *A23L 2/60* | (2006.01) |
| *C07H 1/08* | (2006.01) |
| *A23L 5/20* | (2016.01) |
| *A23L 27/30* | (2016.01) |

(52) U.S. Cl.
CPC .......... *C07H 15/256* (2013.01); *A23L 1/2363* (2013.01); *A23L 2/60* (2013.01); *A23L 5/23* (2016.08); *A23L 27/36* (2016.08); *C07H 1/08* (2013.01); *C07H 15/24* (2013.01)

(58) Field of Classification Search
CPC ............ A23V 2300/14; A23V 2300/24; A23V 2250/262; A23L 1/2366; A23L 1/0152; A23L 1/2363; A23L 2/60; A23L 5/23; A23L 27/36; C07H 1/08; C07H 15/24; C07H 15/256

USPC .............. 426/658, 638; 536/18.1; 204/157.62
See application file for complete search history.

(56) References Cited

U.S. PATENT DOCUMENTS

| | | | | |
|---|---|---|---|---|
| 5,962,678 A | * | 10/1999 | Payzant et al. | 536/128 |
| 6,517,853 B1 | * | 2/2003 | George et al. | 424/405 |
| 7,923,552 B2 | | 4/2011 | Jackson et al. | |
| 2008/0300402 A1 | * | 12/2008 | Yang et al. | 536/128 |
| 2010/0227034 A1 | * | 9/2010 | Purkayastha et al. | 426/302 |
| 2011/0207918 A1 | | 8/2011 | Jackson et al. | |
| 2011/0251380 A1 | | 10/2011 | Jackson et al. | |

FOREIGN PATENT DOCUMENTS

| | | | |
|---|---|---|---|
| CN | 101591367 A | * | 12/2009 |
| CN | 101798329 A | * | 8/2010 |

OTHER PUBLICATIONS

Castro et al "Ultrasound Assisted Crystallization (sonocrystallization)" Ultrasonics Sonochemistry 14 (2007) 717-724.*
Mansour and Takrouri, A New Technology for the Crystallization of Dead Sea Potassium Chloride, Chemical Engineering Communications 2016, pp. 803-810.

* cited by examiner

*Primary Examiner* — Jyoti Chawla
(74) *Attorney, Agent, or Firm* — Thomas | Horstemeyer, LLP

(57) ABSTRACT

There is provided processes for the purification of rebaudioside A from Steviol glycoside compositions, such as Stevia extracts. Also provided are pure compositions and formulations thereof of rebaudioside A with traces amounts of remaining steviol glycosides of less than 1%. Also provided are prepared foods, beverages, medicines and dietary supplements containing pure rebaudioside A.

28 Claims, 12 Drawing Sheets

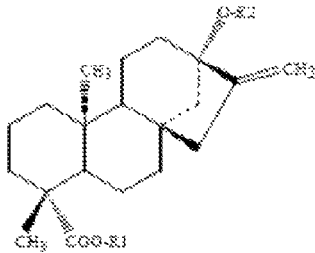

| Compound name | R1 | R2 |
|---|---|---|
| Stevioside | $\beta$-Glc | $\beta$-Glc-$\beta$-Glc(2→1) |
| Rebaudioside A | $\beta$-Glc | $\beta$-Glc-$\beta$-Glc(2→1)<br>\|<br>$\beta$-Glc(3→1) |
| Rebaudioside B | H | $\beta$-Glc-$\beta$-Glc(2→1)<br>\|<br>$\beta$-Glc(3→1) |
| Rebaudioside C | $\beta$-Glc | $\beta$-Glc-$\alpha$-Rha(2→1)<br>\|<br>$\beta$-Glc(3→1) |
| Rebaudioside D | $\beta$-Glc-$\beta$-Glc(2→1) | $\beta$-Glc-$\beta$-Glc(2→1)<br>\|<br>$\beta$-Glc(3→1) |
| Rebaudioside F | $\beta$-Glc | $\beta$-Glc-$\beta$-Xyl(2→1)<br>\|<br>$\beta$-Glc(3→1) |
| Dulcoside A | $\beta$-Glc | $\beta$-Glc-$\alpha$-Rha(2→1) |
| Rubusoside | $\beta$-Glc | $\beta$-Glc |
| Steviolbioside | H | $\beta$-Glc-$\beta$-Glc(2→1) |

Steviol (R1 = R2 = H) is the aglycone of the steviol glycosides.
Glc, Rha and Xyl represent, respectively, glucose, rhamnose and xylose sugar moieties

Fig. 1

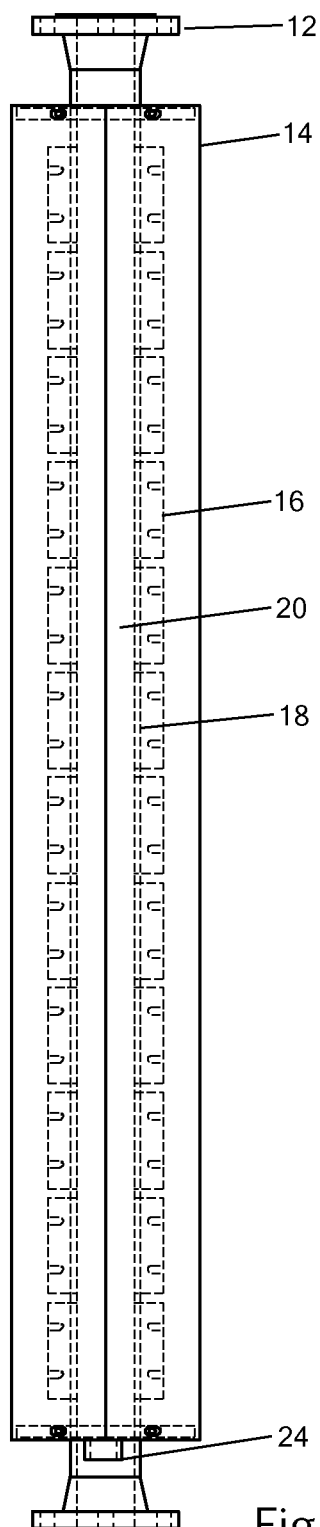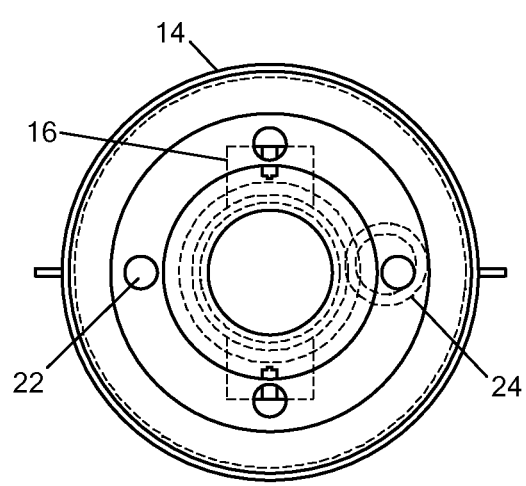
Fig. 5B
Fig. 5A

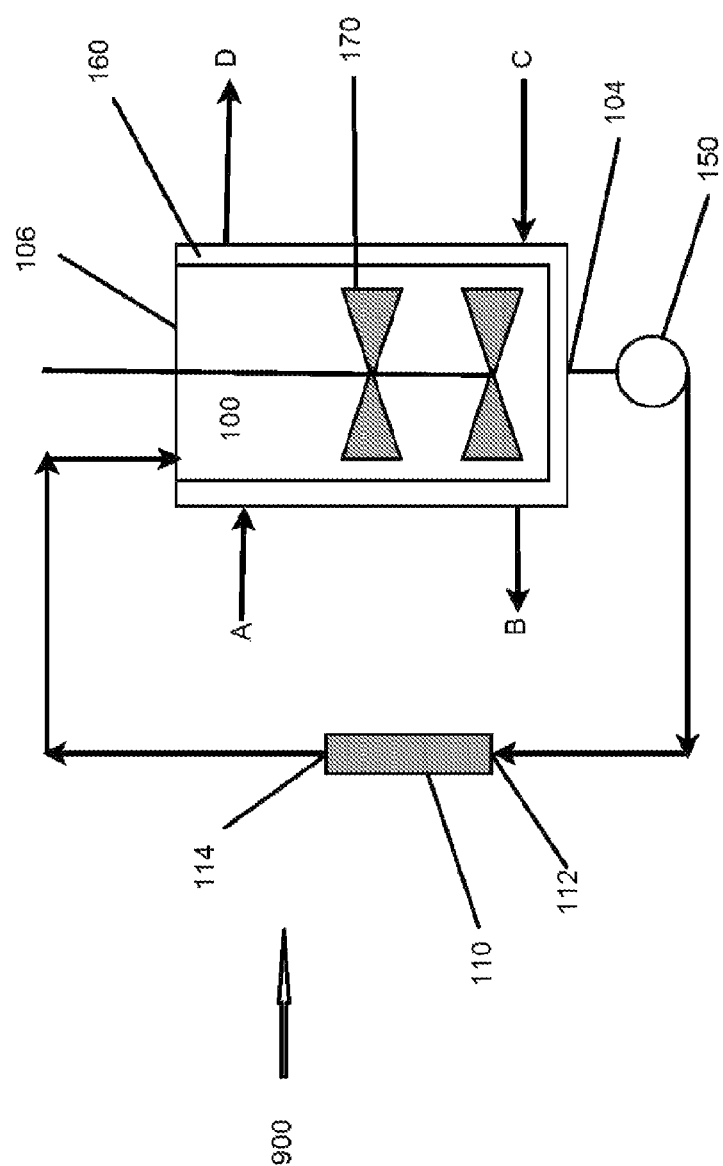

PROCESS FOR THE PURIFICATION OF REBAUDIOSIDE A AND COMPOSITIONS THEREOF

CROSS-REFERENCE TO RELATED APPLICATIONS

This application claims the benefit of Provisional application Ser. No. 61/576,430 filed on Dec. 16, 2011, the entire content of which is incorporated herein by reference.

TECHNICAL FIELD

The present invention relates to a non-caloric sweetener, and more particularly to pure forms of rebaudioside A.

BACKGROUND ART

Rebaudioside A is a steviol glycoside derived from the *Stevia rebaudiana* (Bertoni) plant. Rebaudioside A (13-[(2-O-β-D-glucopyranosyl-3-O-β-Dglucopyranosyl-β-D-glucopyranosyl)oxy]kaur-16-en-18-oic acid, β-D-glucopyranosyl ester), and stevioside (13-[(2-O-β-D-glucopyranosyl-β-D-glucopyranosyl)oxy]kaur-16-en-18-oic acid, β-D-glucopyranosyl ester) are the component glycosides of principal interest for their sweetening property extracted from the *Stevia rebaudiana* plant. *S. rebaudiana* and stevioside have been consumed for hundreds of years by humans, in various countries, as sweeteners in foods and beverages. More recently, rebaudioside A is been predominantly used as a non-caloric sweetener in a variety of conventional food products, such as cereals, energy bars, and beverages at levels consistent with the acceptable daily intake (ADI) of 0-4 mg/kg body weight a day based on steviol content.

In current practice, rebaudioside A is first isolated from the leaves of the Stevia plant in a mixture of steviol glycosides (Stevia extract) at a concentration ranging from about 30-60%. Other glycosides most commonly present in the extract include rebaudioside B, rebaudioside C, rebaudioside D, rebaudioside F, dulcoside A, rubusoside, stevioside and steviolbioside, which are generally present in preparations of steviol glycosides at levels much lower than stevioside or rebaudioside A.

Because these other steviol glycosides carry a bitter after-taste, a whole industry has developed to provide processes to purify rebaudioside A to remove these less desirable glycosides. Predecessors to the present inventors have prepared rebaudioside A compositions having purity levels of more than 96.6% but less than 98.5%, with varying concentrations of the remaining steviol glycosides. However, there remains a need to develop purer rebaudioside A sweetener with better tasting and more readily soluble properties.

SUMMARY OF THE EMBODIMENTS

Thus, the present invention concerns processes for preparing rebaudioside A and compositions thereof at purity of at least 98.7%, more preferably of at least 99.0% and more preferably of at least 99.8%. Further, the present invention concerns the preparation of formulations, food and beverage products, medicines and dietary supplements containing rebaudioside A compositions having purity of at least 98.7%, at least 99.0%, or at least 99.8%.

In one embodiment, the method of purifying rebaudioside A proceeds with the steps of forming a supersaturated solution of a steviol glycoside mixture containing rebaudioside A in a solvent mixture of absolute ethanol and water, and exposing the solution to sonication. In some embodiments, the solvent mixture has about 20% water. In some other embodiments, the solvent mixture has no more than about 2% water. In yet some other embodiments, the solvent mixture has no more than about 1% water. Still, in other embodiments, the solvent mixture has no more than about 0.5% water. In some embodiments, the steviol glycoside mixture is a Stevia extract. In some other embodiments, the steviol glycoside mixture is crude rebaudioside A isolated from a first cycle of crystallization.

In some embodiments, exposure of the supersaturated solution to sonication is performed at below about 60° C. In other embodiments, it is performed at about 40° C. In some embodiments, the exposure to sonication is performed for a continuous period of time for at least about 15 mins, or about 30 mins. In some embodiments, the exposure to sonication is performed in a continuous flow sonication vessel. In some embodiments, the exposure to sonication is performed at a power selected in the range of 20 to 50,000 Watts and at a frequency selected in the range of 30 to 40 kHz. In some embodiments, the exposure to sonication is performed without pulse.

In some embodiments, the process results in the isolation of rebaudioside A having at least 65±1% of rebaudioside A, no more than 25±1% of stevioside and optionally with an impurity profile of no more 6.5±0.1% of rebaudioside C, 1.3±0.1% of rebaudioside F, and no more than 1.0±0.05% of remaining steviol glycosides. In some embodiments, the process results in the isolation of rebaudioside A having at least 75±1% of rebaudioside A, no more than 17±1% of stevioside and optionally with an impurity profile of no more than 6.0±0.1% of rebaudioside C, no more than 1.2±0.1% of rebaudioside F, and no more than 1.0±0.05% of remaining steviol. In some embodiments, the process results in the isolation of rebaudioside A having at least 80±1% of rebaudioside A, no more than 14±1% of stevioside and optionally with an impurity profile of no more than 5.5±0.1% of rebaudioside C, no more than 2.0±0.1% of rebaudioside F, and no more than 1.0±0.05% of remaining steviol.

In other embodiments, the method of purifying rebaudioside A proceeds with the steps of forming a supersaturated solution of a Steviol glycosides mixture comprising at least 65±1% of rebaudioside A, no more than 25±1% of stevioside and optionally with an impurity profile of no more 6.5±0.1% of rebaudioside C, 1.3±0.1% of rebaudioside F, and no more than 1.0±0.05% of remaining Steviol glycosides in a solvent mixture of absolute ethanol and water, and exposing the solution to sonication. In some embodiments, the process results in the isolation of rebaudioside A having at least 98.7±1% of rebaudioside A and optionally with an impurity profile of no more than 0.02±0.005% of rebaudioside B, no more than 0.15±0.01% of rebaudioside C, no more than 0.30±0.02% of rebaudioside F, no more than 0.40±0.05% of Stevioside, no more than 0.030±0.005% of Dulcoside A; no more than 0.040±0.005% of Rubusoside; and no more than 0.010±0.005% of steviolbioside.

In some other embodiments, the process results in the isolation of rebaudioside A having at least 99±1% of rebaudioside A and optionally with an impurity profile of no more than 0.006±0.002% of rebaudioside B; no more than 0.010±0.005% of rebaudioside C; no more than 0.20±0.02% of rebaudioside F; no more than 0.010±0.005% of Stevioside; no more than 0.010±0.005% of Dulcoside A; no more than 0.010±0.005% of Rubusoside; and no more than 0.030±0.005% of Steviolbioside. In some other embodiments, the process results in the isolation of rebaudioside A having at least 99.8±1% of rebaudioside A and optionally with an impurity profile; no more than 0.20±0.02% of rebaudioside F; and rebaudioside B; rebaudioside C, Stevioside, Dulcoside A, Rubusoside, and Steviolbioside remains undetected at a sensitivity level of about 0.006%. In some embodiments, rebaudioside A is produce with rebaudioside F as the sole steviol glycoside impurity.

In another embodiment, the method of purifying rebaudioside A proceeds with the steps of forming a supersaturated solution of a Stevia extract in a solvent mixture of absolute ethanol and water; exposing the solution to sonication; isolating a first composition comprising a crude rebaudioside A, forming a supersaturated solution of the first composition of crude rebaudioside A in a solvent mixture of absolute ethanol and water, exposing the solution to sonication, and isolating a second composition having rebaudioside A with a purity of at least 98.7%.

In another embodiment, the method of purifying rebaudioside A proceeds with the steps of forming a supersaturated solution of a Stevia extract in a solvent mixture of anhydrous ethanol; isolating a first composition comprising a crude rebaudioside A, forming a supersaturated solution of the first composition of crude rebaudioside A in a solvent mixture of ethanol and water, and isolating a second composition having rebaudioside A with a purity of at least 98.7%, 99.0%, 99.5% or 99.9%.

In some embodiments, the method of purifying rebaudioside A proceeds with a preliminary step of drying the Stevia extract so that its water content is no more than 1%, or no more than 0.5%, 0.1% or 0%.

In other embodiments, the formation of a supersaturated solution is first prepared by heating the solution to reflux of the solvent mixture. In some embodiments, the method of purifying crude rebaudioside A proceeds by heating the solution to reflux of the solvent mixture. In some embodiments, the method of purifying rebaudioside A proceeds with absolute ethanol with a water content of no more than 1%. In some embodiments, the method of purifying rebaudioside A proceeds with absolute ethanol with a water content of no more than 0.5%. In some embodiments, the method of purifying rebaudioside A proceeds by forming a supersaturated solution of a Stevia extract in a solvent mixture of absolute ethanol and no more than about 2% water and isolating rebaudioside A. In some other embodiments, the method of purifying rebaudioside A proceeds with a solution of absolute ethanol with 5 to 20% of water In other embodiments, the invention concerns compositions of pure rebaudioside A having at least 98.7±0.1% of rebaudioside A and optionally with an impurity profile of no more than 0.010±0.005% of rebaudioside B, no more than 0.010±0.005% of rebaudioside C, no more than 0.50±0.02% of rebaudioside F, no more than 0.55±0.005% of Stevioside, no more than 0.010±0.005% of Dulcoside A, no more than 0.010±0.005% of Rubusoside, and no more than 0.010±0.005% of Steviolbioside. In some embodiments, the rebaudioside A has rebaudioside F as the sole steviol glycoside impurity.

In other embodiments, the compositions of pure rebaudioside A have at least 98.7±0.1% of rebaudioside A and optionally with an impurity profile of no more than 0.010±0.005% of rebaudioside B, no more than 0.011±0.005% of rebaudioside C, no more than 0.28±0.02% of rebaudioside F, and no more than 0.010±0.005% of Stevioside. In other embodiments, the compositions of pure rebaudioside A have at least 98.7±0.1% of rebaudioside A and optionally with an impurity profile of no more than 0.010±0.005% of rebaudioside B, no more than 0.010±0.005% of rebaudioside C, no more than 0.23±0.02% of rebaudioside F, and no more than 0.010±0.005% of stevioside.

In yet other embodiments, the compositions of pure rebaudioside A have at least 98.7±0.1% of rebaudioside A and optionally with an impurity profile of no more than 0.010±0.005% of rebaudioside B, no more than 0.010±0.005% of rebaudioside C; no more than 0.20±0.02% of rebaudioside F; and no more than 0.010±0.005% of Stevioside.

Still, in other embodiments, the compositions of pure rebaudioside A have at least 98.7±0.1% of rebaudioside A and optionally with an impurity profile of no more than 0.010±0.005% of rebaudioside B, no more than 0.010±0.005% of rebaudioside C, no more than 0.18±0.02% of rebaudioside F, no more than 0.010±0.005% of Stevioside, no more than 0.010±0.005% of Dulcoside A, no more than 0.010±0.005% of Rubusoside, and no more than 0.010±0.005% of Steviolbioside.

In other embodiments, the compositions of pure rebaudioside A have at least 98.7±0.1% of rebaudioside A and optionally an impurity profile of, no more than 0.010±0.005% of rebaudioside C, no more than 0.10±0.02% of rebaudioside F, no more than 0.010±0.005% of Stevioside, no more than 0.010±0.005% of Dulcoside A, no more than 0.010±0.005% of Rubusoside, and no more than 0.010±0.005% of Steviolbioside.

In other embodiments, the compositions of pure rebaudioside A have rebaudioside F as the sole steviol glycoside impurity. In other embodiments, the compositions of pure rebaudioside A have at least 99.0±0.1% of rebaudioside A with rebaudioside F as the sole steviol glycoside impurity. In other embodiments, the compositions of pure rebaudioside A have at least 99.5±0.1% of rebaudioside A with rebaudioside F as the sole steviol glycoside impurity. In other embodiments, the compositions of pure rebaudioside A have at least 99.8±0.1% of rebaudioside A with rebaudioside F as the sole steviol glycoside impurity In other embodiments, the compositions of pure rebaudioside A have at least 99.0±0.1% of rebaudioside A. In other embodiments, the compositions of pure rebaudioside A have at least 99.5±0.1% of rebaudioside A. In other embodiments, the compositions of pure rebaudioside A have at least 99.8±0.1% of rebaudioside A.

In other embodiments, the invention concerns a prepared food containing the pure rebaudioside A composition according to the invention described herein. In some embodiments, rebaudioside A makes up at least 98.7% of all steviol glycosides. In some other embodiments, the rebaudioside A makes up at least 99.0% of all steviol glycosides. In yet other embodiments, the rebaudioside A makes up at least 99.5% of all steviol glycosides. In other embodiments, the rebaudioside A makes up at least 99.8% of all steviol glycosides.

In some embodiments, the prepared food is a beverage such as one selected from coffee, tea, chocolate, fruit juice, milk, milk formula, a protein drink, soft drink, syrup, flat water, and sparkling water.

In some embodiments, the prepared food contains a cereal such as one selected from a breakfast cereal, an energy bar, dough, pastry, a cookie, and bread. In some embodiments, the prepared food contains a vegetable such as one selected from a potato chips, corn chips, sauce, soup, vegetable preserve, and prepared meal. In some embodiments, the prepared food contains a fruit such as one selected from a candied fruit, a dried fruit, a trail mix, a jam, fruit preserve, and a sauce. In some embodiments, the prepared food contains a meat such as one selected from a preserved meat, a prepared meal, a soup, a sausage, and a ground meat. In some embodiments, the prepared food contains seasoning such as one selected from an herb mixed, a salt mix, a spice mix, a soup base, vegetable bouillon extract, meat bouillon extract, a dressing, and a marinade. In some embodiments, the prepared food is a confectionary such as one selected from a hard candy, a popsicle, a caramel, a licorice, a gum, a chewing gum, a toffee, a chocolate, and candy bar. In some embodiments, the prepared food is a dairy such as one selected from milk, fermented milk, yogurt, cream, ice cream, cheese, and egg product.

In other embodiments, the invention concerns the preparation of a sweetener formulation of rebaudioside A comprising the pure rebaudioside A according to embodiments described herein and a consumable acceptable carrier. In some embodiment, in the sweetener formulations, rebaudioside A makes up at least 98.7% of all steviol glycosides and a consumable acceptable carrier. In some embodiments, the formulation contains a composition of rebaudioside A that makes up at least 99.0% of all steviol glycosides. In some embodiments, the formulation contains a composition of rebaudioside A that makes up at least 99.5% of all steviol glycosides. In some embodiments, the formulation contains a composition of rebaudioside A that makes up at least 99.8% of all steviol glycosides.

In some embodiments, the formulation contains water as a carrier. In some embodiments, the formulation contains as a carrier glucose, dextrose, sugar, syrups of sugars, fructose, or a mixture thereof. In some embodiments, the formulation contains a sugar alcohol such as sorbitol, mannitol, maltitol, xylitol, or erythritol as a carrier. In some embodiments, the formulation contains corn syrup as a carrier. In some embodiments, the formulation contains a dextran or a dextrin as a carrier. In some embodiments, the formulation contains a starch as a carrier. In some embodiments, the formulation contains whey as a carrier. In some embodiments, the formulation contains a fatty acid as a carrier. In some embodiments, the formulation contains a wax as a carrier. In some embodiments, the formulation contains a gum as a carrier. In some embodiments, the formulation contains a mixture of two or more of these carriers. Examples of these carriers are well known in the art.

In some embodiments, the formulation is prepared in the form of a powder. In some embodiments, the formulation is prepared in the form of a tablet. In some embodiments, the formulation is prepared in the form of a syrup. In some embodiments, the formulation is prepared in the form of granules.

In other embodiments, the invention concerns a medicine or dietary supplement containing a pure rebaudioside A according to embodiments described herein. The medicine or dietary supplement is a syrup, a chewable tablet, a powder mix, granules, or a herbal mix.

BRIEF DESCRIPTION OF THE DRAWINGS

The foregoing features of embodiments will be more readily understood by reference to the following detailed description, taken with reference to the accompanying drawings.

FIG. 1 is a representation of the chemical structures of the nine known steviol glycosides.

FIGS. 5A and 5B are depiction of the front and top views respectively of an embodiment of an ultrasonic reactor.

FIG. 9 is a depiction of an embodiment of a manufacturing assembly.

DETAILED DESCRIPTION OF SPECIFIC EMBODIMENTS

Definitions. As used in this description and the accompanying claims, the following terms shall have the meanings indicated, unless the context otherwise requires:

Anhydrous ethanol as described herein has a minimal water content, preferably at or below 0.5%, preferably about 0%.

Relating to the description of the purity levels and the content of components in the compositions, percentages are determined by the integration of peaks in HPLC chromatograms, that is the area under the curve of an identified peak of interest over the sum of the area under the curve of all peaks in a chromatogram. Accuracy of the measurements, with the number of significant figures in a stated value, is dependent on the sensitivity of the detector and the resolution of the peaks.

Referring to FIG. 1, rebaudioside A and stevioside (a steviol glycoside closely related) are typically identified as the principal sweetening constituents found in *S. rebaudiana* and are accompanied by smaller amounts of other steviol glycosides: rebaudioside B, rebaudioside C, rebaudioside D, rebaudioside F, dulcoside A, rubusoside and steviolbioside. It has proven difficult to produce pure rebaudioside A without the presence of mixtures of these remaining steviol glycosides.

There is provided herein various embodiments of a process for isolating rebaudioside A from a Stevia extract, and compositions of purified rebaudioside A isolated by any of the embodiments of processes according to the claimed invention. The purified rebaudioside A according to embodiments of the claimed invention has improved solubility (is readily soluble in water), greater stability and is better tasting.

Figure 2A:
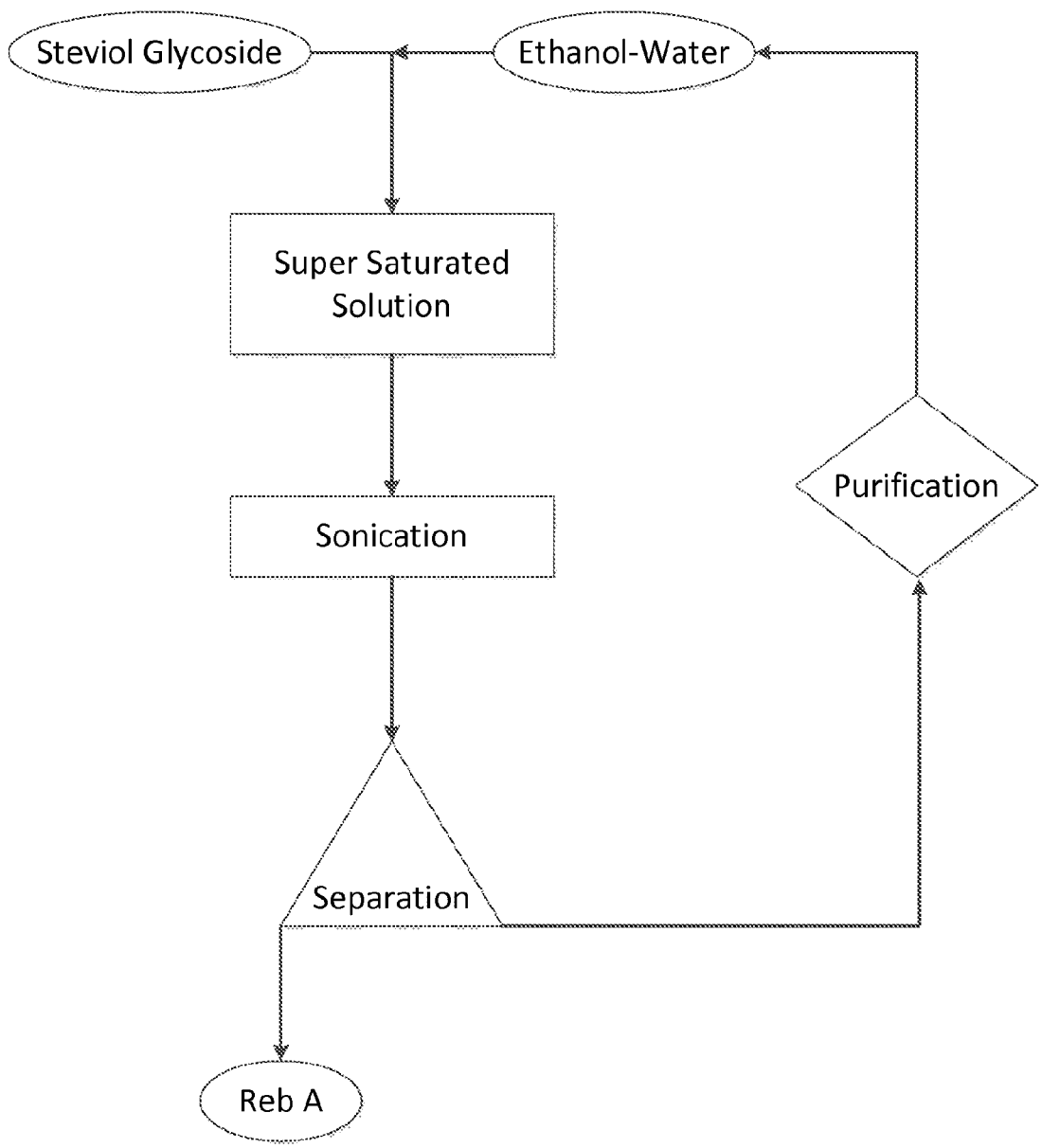
FIGS. 2A and 2B are flow diagrams of embodiments of a process according to the invention.

Referring to FIG. 2A, in one embodiment of the invention, a mixture of steviol glycosides containing rebaudioside A is first mixed with a solvent mixture of ethanol and water to form a supersaturated solution. The supersaturated solution is exposed to sonication to trigger nucleation, thus initiating crystallization of rebaudioside A. The crystals of rebaudioside A are then separated from the solvent mixture. Optionally the crystals are dried. Optionally, the solvent may be purified and recycled in the process. Alternatively, the supersaturated solution is left to cool without sonication.

In one embodiment, the initial steviol glycoside mixture may be a Stevia extract. In a stevia extract, rebaudioside A is commonly present at a concentration of about 30-60%. In another embodiment, the steviol glycoside mixture may be a crude rebaudioside A containing 60-80% of rebaudioside A and about 10-30% of stevioside.

In some embodiment the solvent is anhydrous ethanol. In other embodiments, the solvent is a mixture of ethanol with 5-20% water.

Figure 2B:
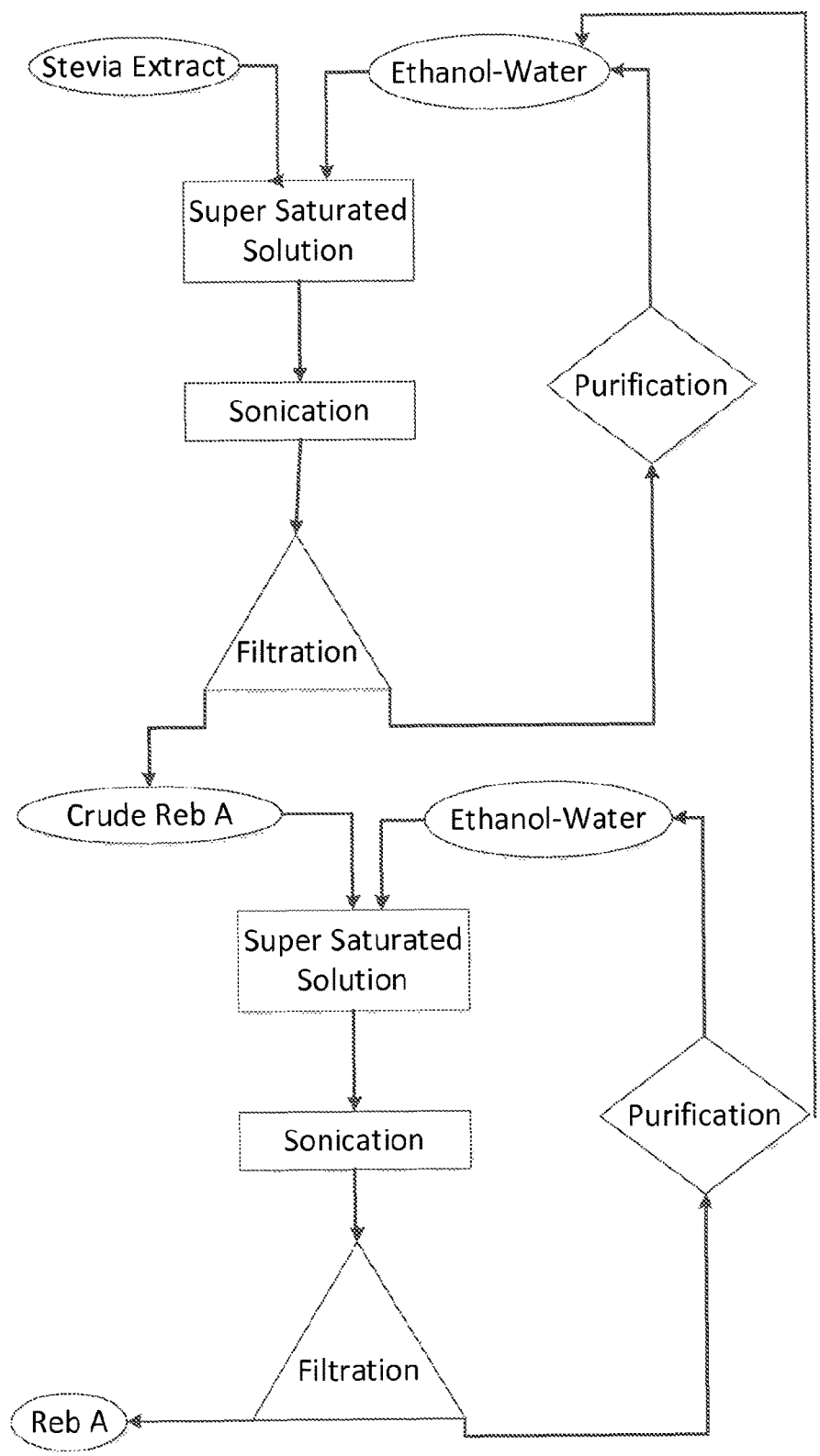

Referring to FIG. 2B, in one embodiment of the invention, the process of crystallization may be repeated to produce pure rebaudioside A. In a first cycle, Stevia extract mixture is first mixed with anhydrous ethanol with no more than 2% water, or preferably no more than 1% water (that is 0%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2%) to form a supersaturated solution. Optionally, the supersaturated solution is exposed to sonication to trigger nucleation, thus initiating crystallization of rebaudioside A. Crystals of crude rebaudioside A comprising about 60-80% rebaudioside A and about 10-30% of stevioside are then separated from the solvent mixture. Optionally, the solvent may be purified and recycled in the process.

The crystals of crude rebaudioside A isolated from the first cycle of crystallization are then subjected to another cycle, that is, they are recrystallized. The crystals are mixed with a solvent mixture of absolute ethanol with about 5-20% water, or preferably about 10-15% water, (that is 5%, 6%, 7%, 8%, 9%, 10%, 11%, 12%, 13%, 14%, 15%, 16%, 17%, 18%, 19%, or 20%) to form a supersaturated solution. Optionally, the supersaturated solution is exposed to sonication to trigger nucleation, thus initiating crystallization of rebaudioside A. Crystals of pure rebaudioside A comprising about 99±1% rebaudioside A, more preferably 98.70 to 99.9%±0.1% (that is 98.7%, 98.8%, 98.9%, 99.0%, 99.1%, 99.2%, 99.3%, 99.4%, 99.5%, 99.6%, 99.7%, 99.8%, or 99.9%) are then separated from the solvent mixture. Optionally, the solvent may be purified and recycled in the process.

Referring to FIGS. 2A and 2B, in some embodiments, sonication is applied with a probe in a vessel for an extended period of time sufficient to trigger nucleation and crystallization. For example, sonication may be applied for periods ranging of 5 mins. to an hour, preferably 15-30 mins (that is for 5 mins, 10 mins, 15 mins, 20 mins, 25 mins, 30 mins, 35 mins, 40 mins, 45 mins, 50 mins, 55 mins, or 60 mins). In some embodiments, sonication is applied at a power intensity of 20-40 Watt per liter, preferably 30 Watt per liter (that is 20 W/l, 21 W/l, 22 W/l, 23 W/l, 24 W/l, 25 W/l, 26 W/l, 27 W/l, 28 W/l, 29 W/l, 30 W/l, 31 W/l, 32 W/l, 33 W/l, 34 W/l, 35 W/l, 36 W/l, 37 W/l, 38 W/l, 39 W/l, or 40 W/l). In some embodiments, sonication is applied at an amplitude of about 20-40 kHz, preferably 30-40 kHz (that is 20 kHz, 21 kHz, 22 kHz, 23 kHz, 24 kHz, 25 kHz, 26 kHz, 27 kHz, 28 kHz, 29 kHz, 30 kHz, 31 kHz, 32 kHz, 33 kHz, 34 kHz, 35 kHz, 36 kHz, 37 kHz, 38 kHz, 39 kHz, or 40 kHz).

Referring to FIGS. 5 to 9, in some embodiments, sonication is applied as the supersaturated solution is pumped through a flow-through vessel equipped with ultrasonic emitters 16. The various parameters such as flow rate, period of time and power used to conduct the sonication are adjusted with the size of the batch such that sonication is applied with the total energy transferred of from about 15 to 25 KJ per liters, such as 15 KJ/l, 16 KJ/l, 17 KJ/l, 18 KJ/l, 19 KJ/l, 20 KJ/l, 21 KJ/l, 22 KJ/l, 23 KJ/l, 24 KJ/l, and 25 KJ/l. Such adjustments may be easily performed by a person skilled in the art apprised of the present disclosure. For example, the sonication power may be set to deliver from about 0.5 kW to 100 kW depending on the size of the sonicator vessel and the flow rate, such as about 0.5 kW, 1 kW, 2 kW, 3 kW, 4 kW, 5 kW, 6 kW, 7 kW, 8 kW, 9 kW, 10 kW, 15 kW, 20 kW, 25 kW, 30 kW, 35 kW, 40 kW, 45 kW, 50 kW, 55 kW, 60 kW, 65 kW, 70 kW, 75 kW, 80 kW, 85 kW, 90 kW, 95 kW, and 100 kW. Flow rates may be set as slow as 0.030 l/s to as fast as 10 l/s, such as about 0.03 l/s, 0.05 l/s, 0.07 l/s 0.09 l/s, 0.1 l/s, 0.2 l/s, 0.3 l/s, 0.4 l/s, 0.5 l/s, 0.6 l/s, 0.7 l/s, 0.8 l/s, 0.9 l/s, 1 l/s, 2 l/s, 3 l/s, 4 l/s, 5 l/s, 6 l/s, 7 l/s, 8 l/s, 9 l/s, and 10 l/s.

Figure 3A:
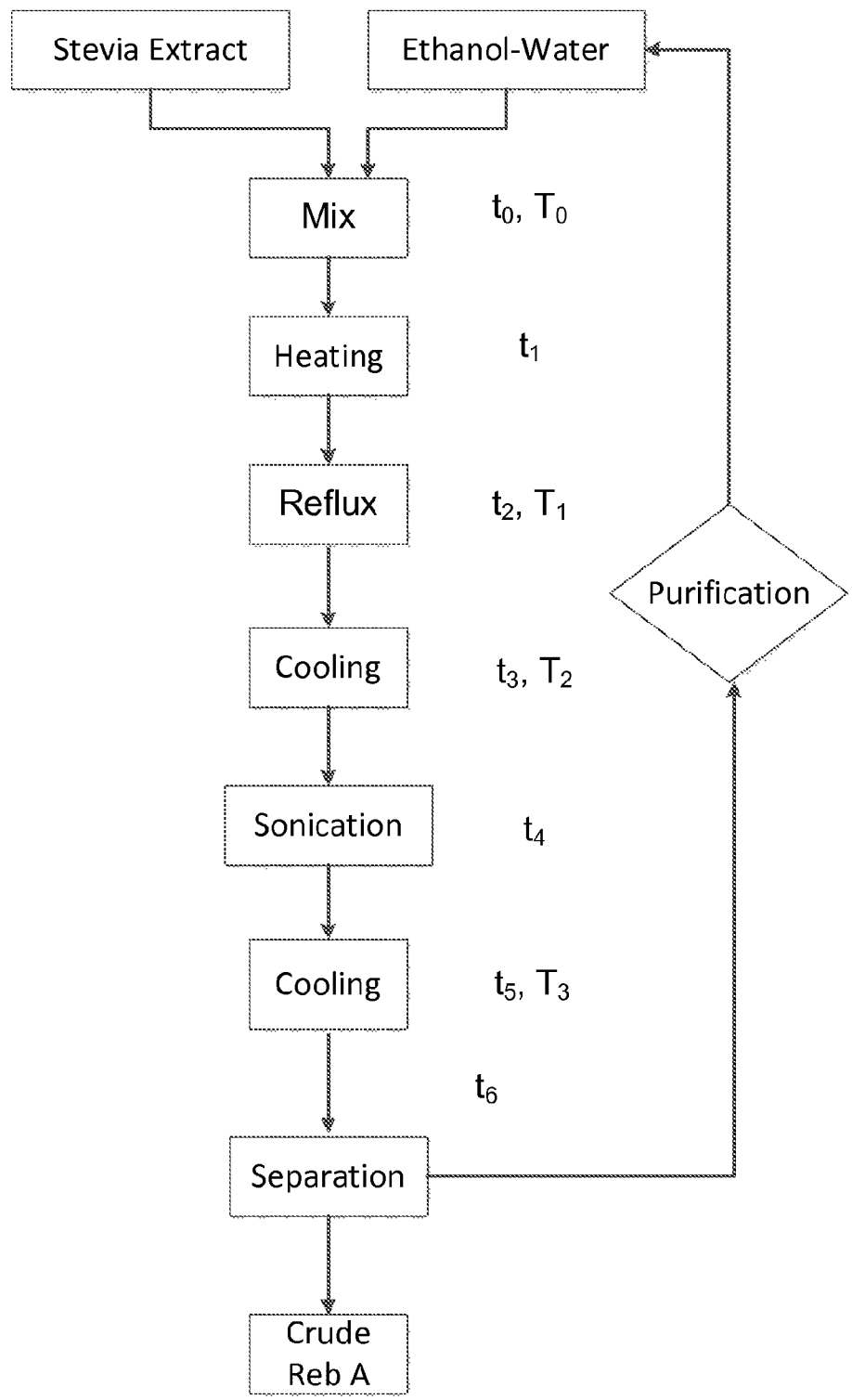
FIGS. 3A and 3B are flow diagrams of embodiments of a process according to the invention.

Referring to FIG. 3A, in one embodiment of the invention, a mixture of Stevia extract containing rebaudioside A is first mixed with a solvent mixture of ethanol and water as described above to form a solution at an initial temperature $T_0$ for a period of time $t_0$. The solution is then heated over a period of time ($t_1$) until it reaches reflux ($T_1$). Reflux is maintained for another period of time ($t_2$), and allowed to cool to a temperature $T_2$ over a period of time ($t_3$). As the solution cools, the solution is exposed to sonication for a period of time ($t_4$) to trigger nucleation, thus initiating crystallization of rebaudioside A. The slurry of crystals and mother liquor is then cooled further to a low temperature $T_3$ over a period of time $t_5$ and maintained at $T_3$ for a period of time $t_6$ to allow the crystals of crude rebaudioside A to mature. The crystals of crude rebaudioside A are then separated from the mother liquor, such as by filtration or centrifugation. Optionally, the solvent and the steviol glycosides in the mother liquor may be purified and the solvent recycled in the process.

Figure 3B:
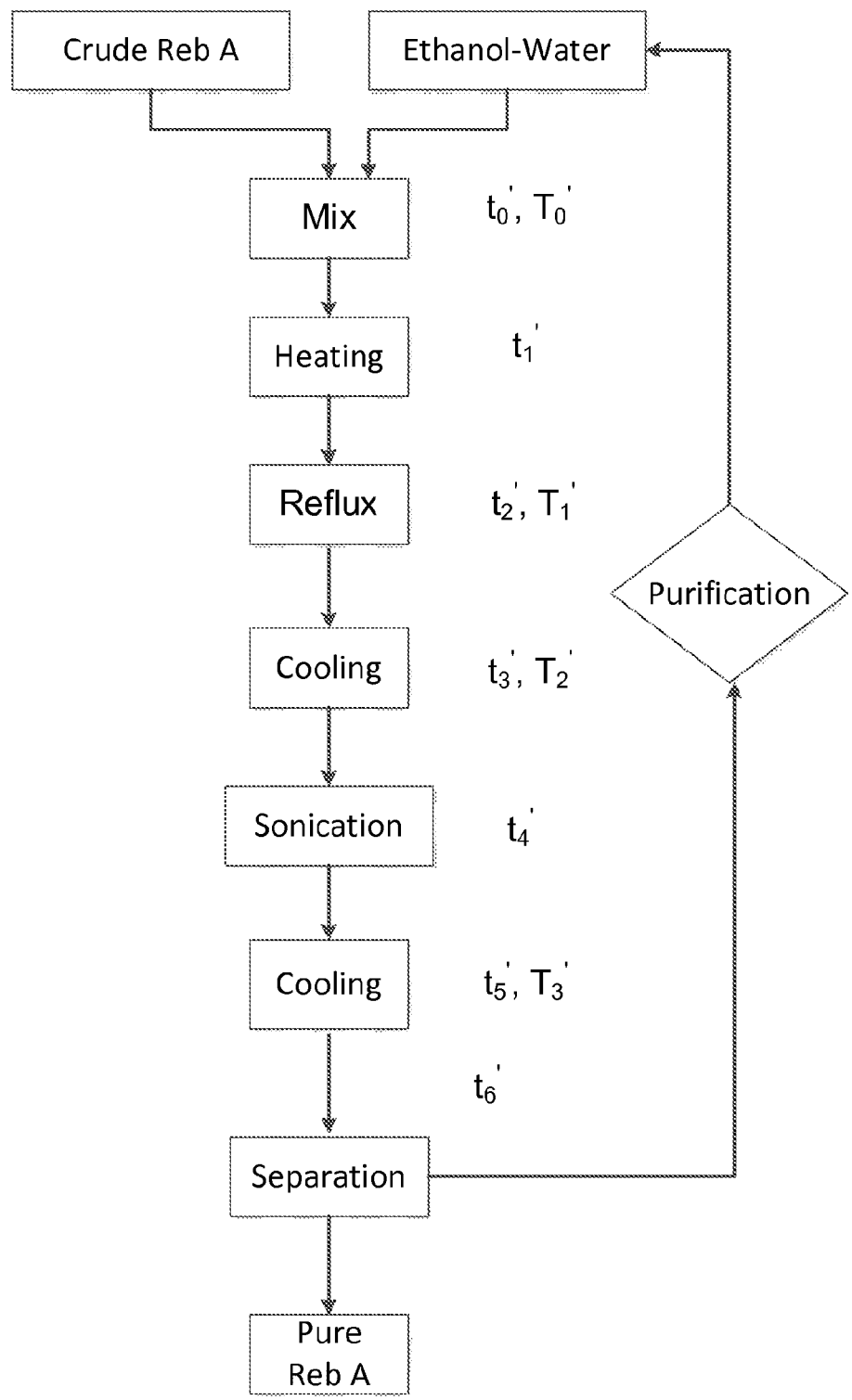

Referring to FIG. 3B, in another embodiment of the invention, the process of crystallization may be repeated to produce pure rebaudioside A. The crystals of crude rebaudioside A isolated from the first cycle of crystallization are then subjected to another cycle, that is, they are recrystallized. The crystals are mixed with an aqueous mixture of absolute ethanol, as described above, to form a solution at an initial temperature $T_0'$ for a period of time $t_0'$. The solution is then heated over a period of time ($t_1'$) until it reaches reflux ($T_1'$). Reflux is maintained for another period of time ($t_2'$), and allowed to cool to a temperature $T_2'$ over a period of time ($t_3'$). As the solution cools, the solution is exposed to sonication for a period of time ($t_4'$) to trigger nucleation, thus initiating crystallization of rebaudioside A. The slurry of crystals and mother liquor is then cooled further to a low temperature $T_3'$ over a period of time $t_5'$ and maintained at $T_3'$ for a period of time $t_6'$ to allow the crystals of crude rebaudioside A to mature. The crystals of pure rebaudioside A are then separated by filtration from the mother liquor. Alternatively, the crystals may be separated from the mother liquor by centrifugation. Optionally, the solvent and the steviol glycosides in the mother liquor may be purified and recycled in the process. The crystals of pure rebaudioside A may be washed with absolute ethanol to eliminate the mother liquor still wetting the crystals.

The periods of time identified above may be selected from the following periods. For $t_0$ or $t_0'$, the period may be in a range of about 10 to 40 mins, preferably 25 mins (that is about 10 mins, 15 mins, 20 mins, 25 mins, 30 mins, 35 mins, or 40 mins). For $t_1$ or $t_1'$, the period may be in a range of about 20 to 40 mins, preferably 30 mins (that is about 20 mins, 25 mins, 30 mins, 35 mins, or 40 mins). For $t_2$ or $t_2'$, the period may be in a range of about 20 to 40 mins, preferably 30 mins (that is about 20 mins, 25 mins, 30 mins, 35 mins, or 40 mins). For $t_3$ or $t_3'$, the period may be in a range of about 10 to 20 mins (that is about 10 mins, 11 mins, 12 mins, 13 mins, 14 mins, 15 mins, 16 mins, 17 mins, 18 mins, 19 mins, or 20 mins). For $t_4$ or $t_4'$, the period may be in a range of about 5 mins to an hour as described above, or preferably of about 20 to 40 mins, preferably 30 mins (that is about 20 mins, 25 mins, 30 mins, 35 mins, or 40 mins). For $t_4$ or $t_4'$, in the case of a process using a flow through device, the period of time by which the entire batch is passed though the ultrasonic reactor may be in a range of about 1-30 hours (that is about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, 25 hrs, 26 hrs, 27 hrs, 28 hrs, 29 hrs, or 30 hrs). For $t_5$ or $t_5'$, the period may be in a range of about 1-20 hours (that is about 1 hr, 2 hrs, 3 hrs, 4 hrs, 5 hrs, 6 hrs, 7 hrs, 8 hrs, 9 hrs, 10 hrs, 12 hrs, 13 hrs, 14 hrs, 15 hrs, 16 hrs, 17 hrs, 18 hrs, 19 hrs, or 20 hrs). For $t_0$ or $t_6'$, the period may be in a range of about 1-30 hours (that is about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, 25 hrs, 26 hrs, 27 hrs, 28 hrs, 29 hrs, or 30 hrs).

The temperatures identified above may be selected as follows. For $T_0$ or $T_0'$, the temperature may be in a range of 15-30° C. (that is 15° C., 16° C., 17° C., 18° C., 19° C., 20° C., 21° C., 22° C., 23° C., 24° C., 25° C., 26° C., 27° C., 28° C., 29° C., 20° C., or 30° C.). For $T_1$ or $T_1'$, the temperature may be in a range of 40-78° C. (that is 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., or 78° C.). For $T_2$ or $T_2'$, the temperature may be in a range of 40-60° C. (that is 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., or 60° C.). For $T_3$ or $T_3'$, the temperature may be in a range of −5 to 20° C. (that is −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C.).

Figure 4A:
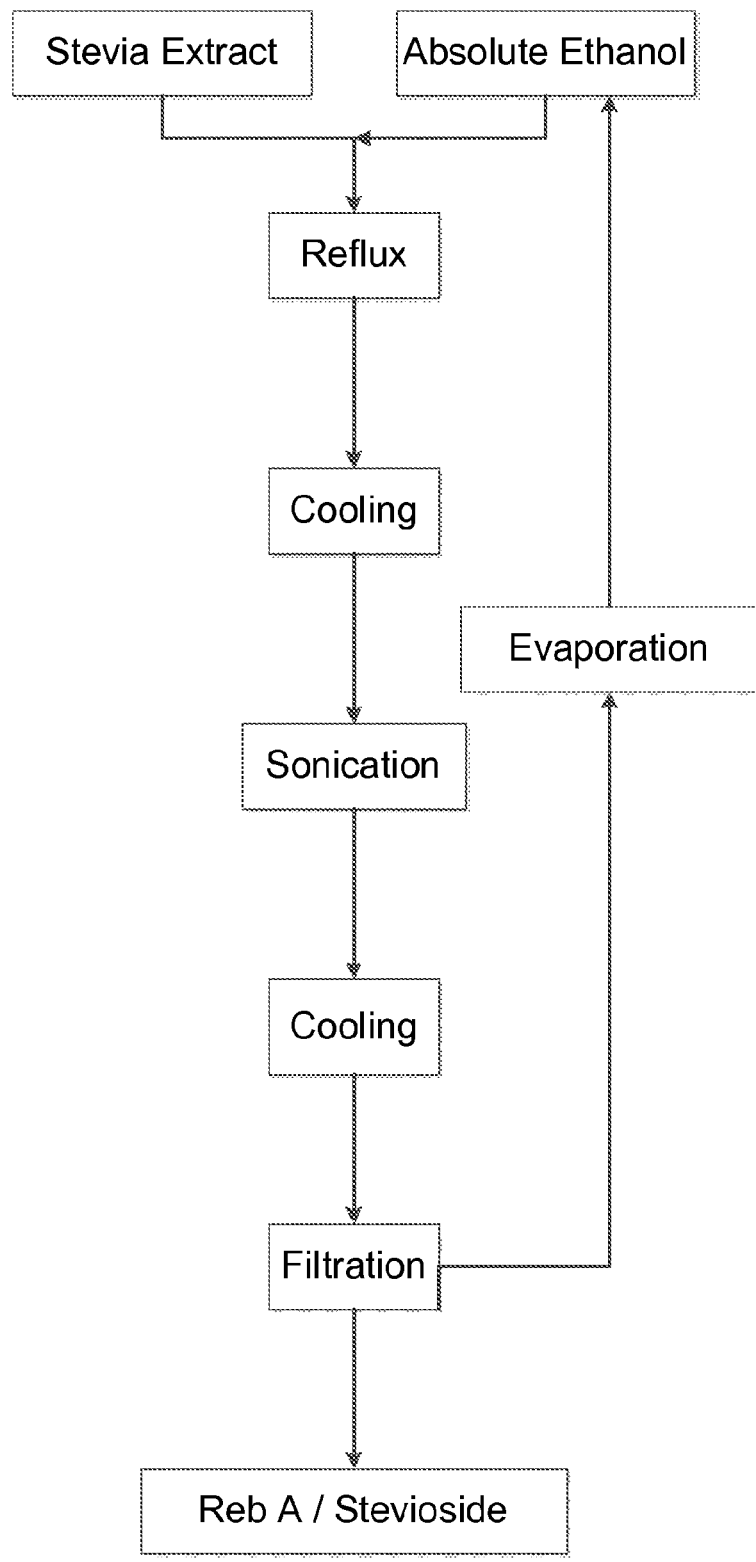
FIGS. 4A and 4B are flow diagrams of embodiments of a process according to the invention.
Figure 4B:
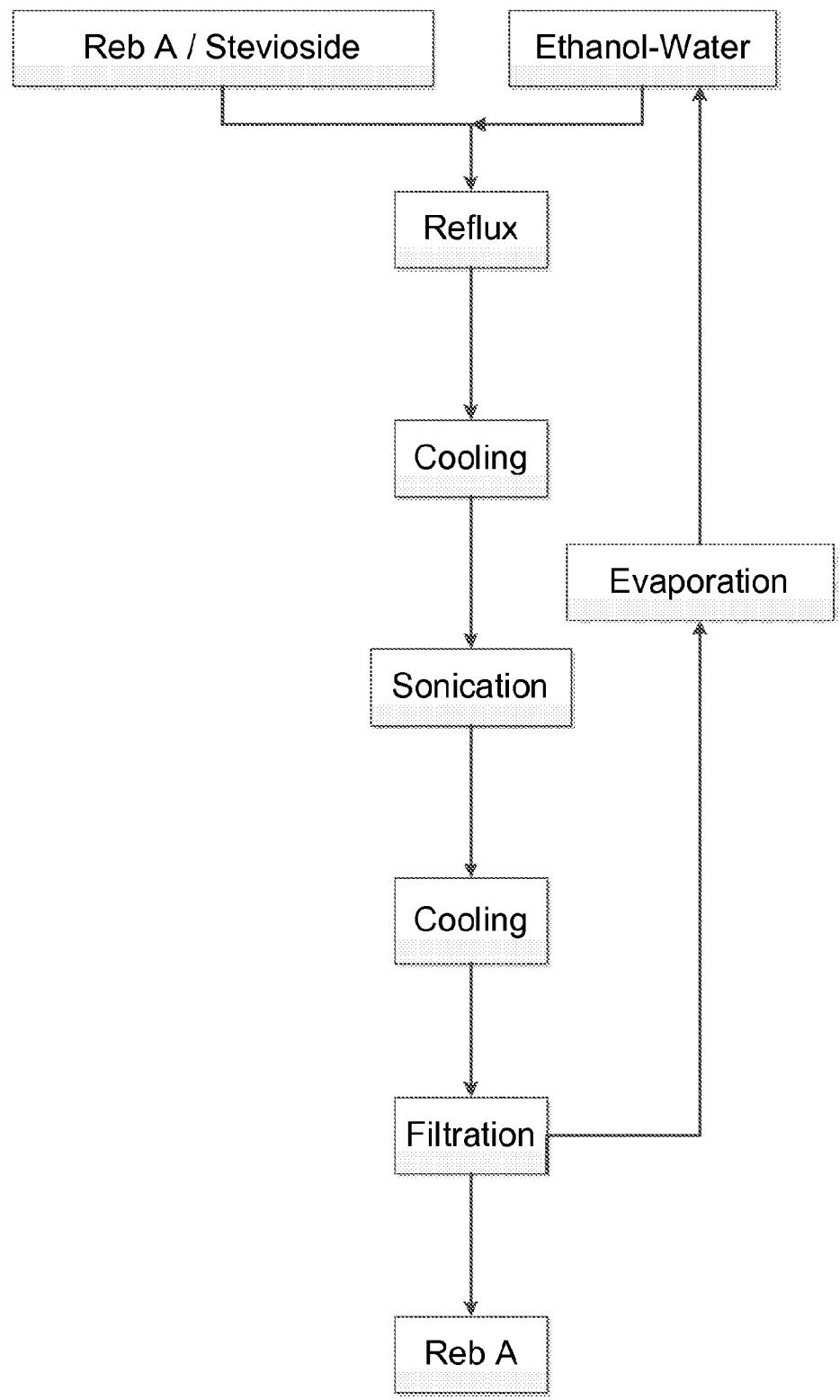

Referring to FIGS. 4A and 4B, in yet another embodiment of the invention, rebaudioside A may be isolated in a pure form from a Stevia extract in two rounds of crystallization as described previously for FIGS. 3A and 3B. The mixture of Stevia extract in the first round, of crude rebaudioside A in the second round is first heated to reflux in anhydrous ethanol (FIG. 4A) or mixture of ethanol and water (FIG. 4B), respectively. The ethanol is recovered from the mother liquors by evaporation, and when used in the first cycle, dried to a water content of no more than 1%, preferably no more than 0.1%.

Referring to FIG. 5A to 5D, in an embodiment of the invention, sonication may be conducted in a flow-through ultrasonic reactor 10, having an elongated reaction chamber 20 defined by a tubular wall 18. At both ends of the reaction chamber 20 are located an inlet and outlet 12 which can be connected with pipes to holding tanks where the heating and cooling of the mixtures are conducted. On the outside wall 18 of the reaction chamber 20, two series of emitters 16 are disposed on opposite sides of the tubular wall 18. Alternatively, one to eight rows of emitters 16 may be used circumferentially, in lines, in alternance or in a helical fashion. The emitters 16 are covered by an outer jacket 14.

The ultrasonic reactor may come in various sizes, power and amplitude to adjust to the size of the batches to be processed. The chamber may be sufficiently long and wide to accommodate various quantities of liquid or slurry of crystals, from about 1 to 50 liters and flow rates as slow as about 72 liters per hour to as fast as about 36,000 liters per hour (i.e. 0.020 to 10 liters per seconds).

Figure 6:
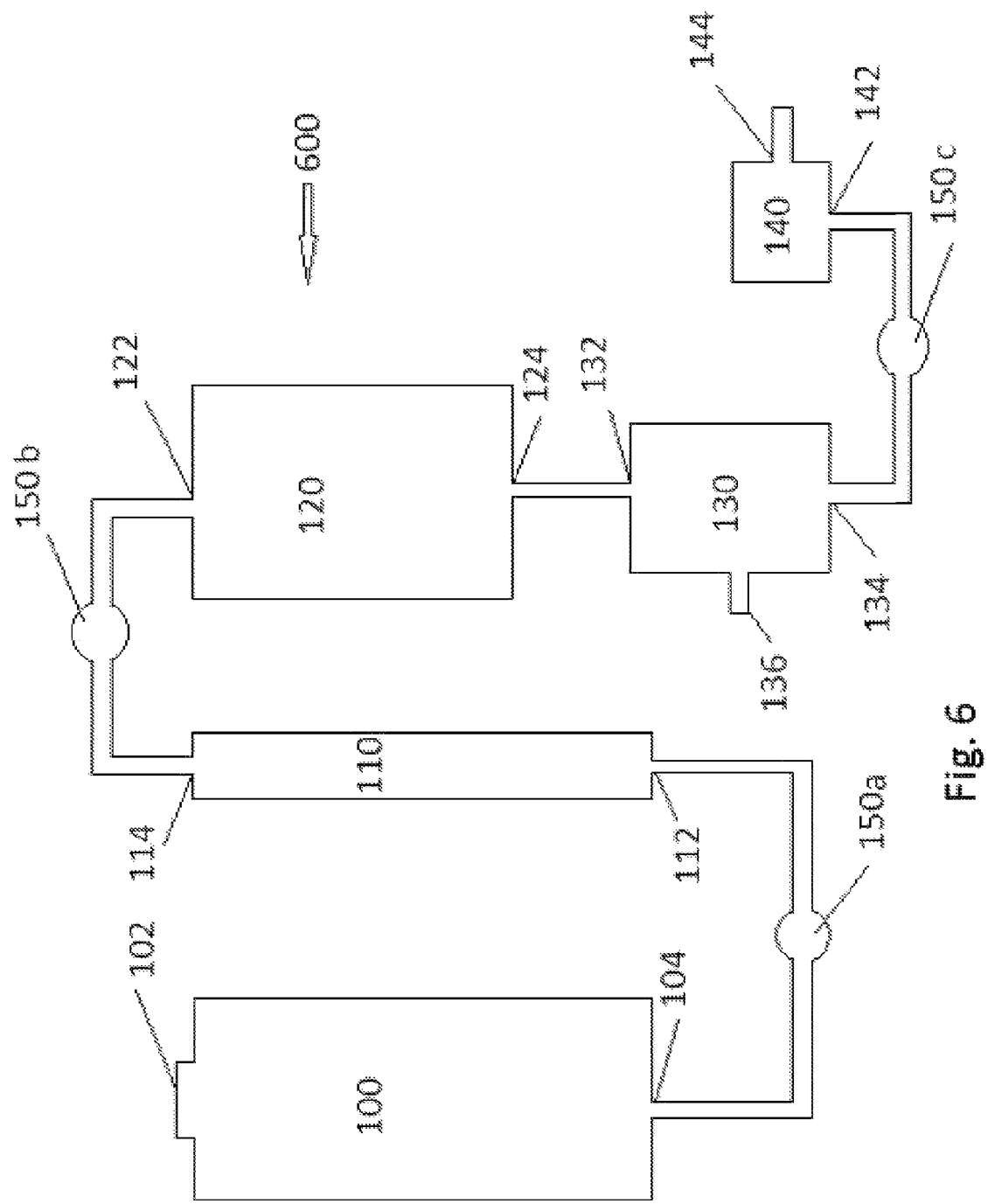
FIG. 6 is a depiction of an embodiment of a manufacturing assembly.

Referring to FIG. 6, in an embodiment of the invention, the process may be conducted in a manufacturing assembly 600. In a reactor 100, the composition containing rebaudioside A to be purified and the solvent are added through inlet 102. The mixture may be stirred and heated (components not shown), and once the mixture has reached the desired temperature, the mixture is sent through outlet 104 with a pump 150a to the inlet 112 of an ultrasonic reactor 110. The mixture is then transferred through outlet 114 to a cooling tank 120 through inlet 122 with a pump 150b, and held there for a period of time until the crystals of rebaudioside A have matured. The slurry of crystals is then transferred in a filtration tank 130 where the solvent is removed through outlet 134. The crystals are recovered through port 136. The solvent is optionally sent with a pump 150c to a distillation unit 140, with an inlet 142 and outlet 144.

Figure 7:
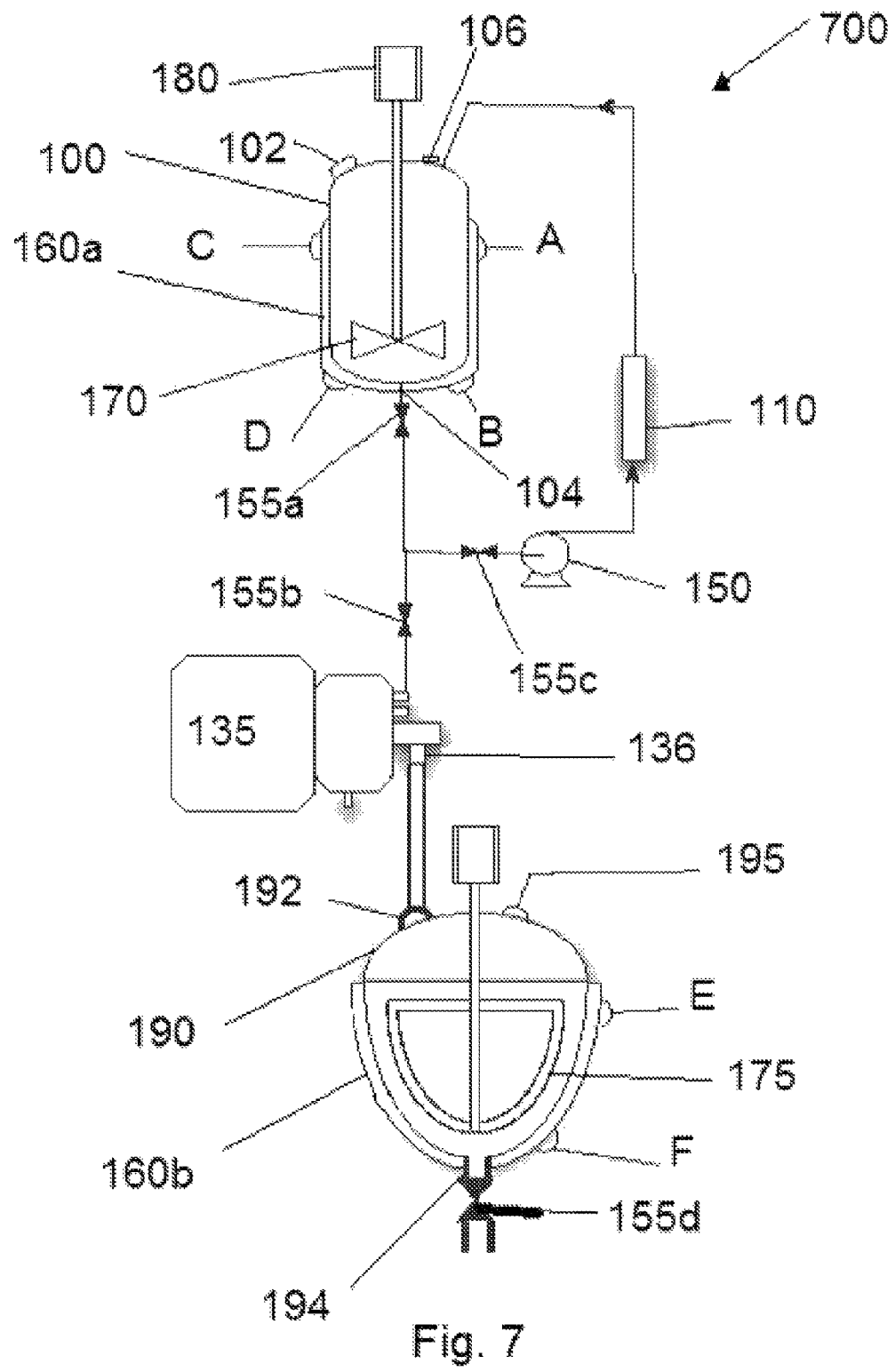
FIG. 7 is a depiction of an embodiment of a manufacturing assembly.

Referring to FIG. 7, in another embodiment of the invention, the process may be conducted in a manufacturing assembly 700. In a reactor 100, the composition containing rebaudioside A to be purified is added through inlet 102 and the solvent is added through inlet 106. The mixture may be stirred with stirrer 170 driven by a motor 180, and heated with a heat exchanger element 160a, within which is circulated steam from inlet A and out outlet B. Once the mixture has reached the desired temperature, the mixture is sent through outlet 104 with a pump 150 to the inlet 112 of an ultrasonic reactor 110. The mixture is then transferred through outlet 114 back to the reactor 100 until a sufficient amount of crystals of rebaudioside A are formed. The mixture may then be cooled with the heat exchanger element 160a, within which cold water is circulated from inlet C and out outlet D, and kept at a low temperature until the crystals of rebaudioside A have matured. The slurry of crystals may then be transferred to a centrifugation vessel 135 where the solvent is removed and a wet cake of the crystals is discharged from port 136. The solvent is optionally sent to a distillation unit (not shown). The wet cake is then transferred to a vacuum drier 190 equipped with a heating heat exchanger 160b, within which is circulated steam from inlet E and out outlet F through inlet 192 while the crystals are slowly agitated with stirrer 175. A vacuum source 195 is connected to the drier to remove the solvent and water content. Movement of fluids, slurries and crystals is controlled by valves 155a, 155b, 155c, and 155d.

Figure 8:
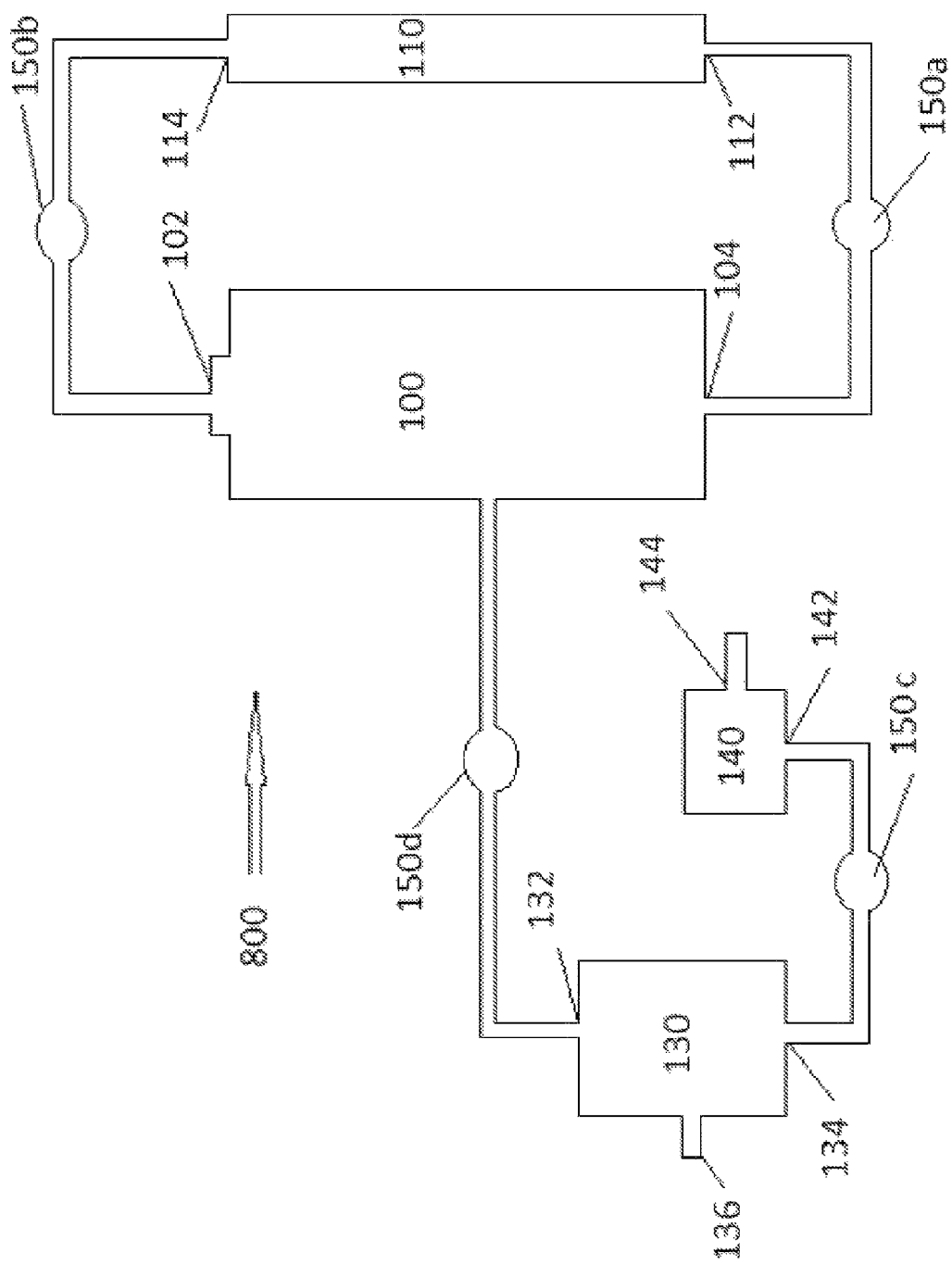
FIG. 8 is a depiction of an embodiment of a manufacturing assembly.

Referring to FIG. 8, in an embodiment of the invention, the process may be conducted in a manufacturing assembly 800. In a reactor 100, the composition containing rebaudioside A to be purified and the solvent are added through inlet 102. The mixture may be stirred (component not shown), and heated with a heat exchanger element 160, and once the mixture has reached the desired temperature, the mixture is sent through outlet 104 with a pump 150a to the inlet 112 of an ultrasonic reactor 110. The mixture is then transferred through outlet 114 back to the reactor until a sufficient amount of crystals of rebaudioside A are formed. The mixture may then be cooled with the heat exchanger element 160, and kept at a low temperature until the crystals of rebaudioside A have matured. The slurry of crystals is then transferred with a pump 150d in a filtration tank 130 where the solvent is removed through outlet 134. The crystals are recovered through port 136. The solvent is optionally sent with a pump 150c to a distillation unit 140, with an inlet 142 and outlet 144.

Referring to FIG. 9, in an embodiment of the invention, the process may be conducted in a manufacturing assembly 900. In a reactor 100, the composition containing rebaudioside A to be purified and the solvent are added through an opening 106. The mixture may be stirred with a stirrer 170, and heated with a heat exchanger element 160, within which is circulated steam from inlet A and out outlet B. Once the mixture has reached the desired temperature, the mixture is sent through outlet 104 with a pump 150 to the inlet 112 of an ultrasonic reactor 110. The mixture is then transferred through outlet 114 back to the reactor until a sufficient amount of crystals of rebaudioside A are formed. The mixture may then be cooled with the heat exchanger element 160, within which cold water is circulated from inlet C and out outlet D, and kept at a low temperature until the crystals of rebaudioside A have matured. The slurry of crystals may then be transferred to a filtration or centrifugation vessel where the solvent is removed and the crystals are recovered. The mother liquor may optionally be sent to a distillation unit to recover and recycle the solvent.

Further embodiments of the invention concern the preparation of food products containing the pure rebaudioside A compositions or formulations described above. In some embodiments, the food product may be a beverage. The beverage may be a liquid or dry mix preparation of coffee, tea, or chocolate, a protein drink, a soft drink, a fruit juice, syrup, flat water, or sparkling water.

In some other embodiments the food product may contain a cereal, a vegetable, a fruit, a meat, a seasoning, a confectionary, or a diary. For example, the cereal may be a breakfast cereal, an energy bar, a cookie, or bread; the vegetable may be from a potato chips, corn chips, sauce, soup, vegetable preserve, or prepared meal; the fruit may be a candied fruit, a dried fruit, a trail mix, a jam, fruit preserve, or a sauce; the meat may be a preserved meat, a prepared meal, a soup, a sausage, or a ground meat; the seasoning may be an herb mixed, a salt mix, a spice mix, a soup base, vegetable bouillon extract, meat bouillon extract, a dressing, or a marinade; the confectionary may be a hard candy, a popsicle, a caramel, a licorice, a gum, a chewing gum, a toffee, a chocolate, or candy bar; the dairy may be milk, fermented milk, yogurt, cream, ice cream, cheese, or eggnog.

In some embodiments of the invention, pure rebaudioside A according to the invention is formulated as a sweetener with a consumable carrier in the form of a tablet, a powder, a syrup, or a granule. In some embodiments, the formulation of pure rebaudioside A is prepared from a composition where rebaudioside A makes up at least 98.7% of all steviol glycoside, at least 99.0% of all steviol glycosides, at least 99.5% of all steviol glycosides, or at least 99.8% of all steviol glycosides.

In some embodiments, the consumable carrier is prepared with water, glucose, sugar, syrups of sugars, fructose, dextrose, sugar alcohols such as sorbitol, mannitol, maltitol, xylitol, or erythritol, corn syrup, a dextran, a dextrin, a starch, whey, a fatty acid, a wax, or a gum or a mixture thereof.

In yet some other embodiments, the sweetener is added to a medicine or dietary supplement. The medicine or dietary supplement may be a syrup, a chewable tablet, a powder mix, granules, or a herbal mix.

In some embodiments the rebaudioside A formulation is applied to food products, medicine or dietary supplements by spray drying, mixing, or soaking.

Preparation of the above foods, beverages, medicines and dietary supplement with the desired palatable sweetening quality is well within the skill of the ordinary artisan. Rebaudioside A may be admixed with the foods, beverages, medicines or dietary supplements at a ratio of about 1 µg to 10 mg per gram of food, beverage, medicine or dietary supplement, such as about 1-10 µg, 10-50 µg, 50-100 µg, 0.1-0.5 mg, 0.5-1 mg, 1-5 mg, or 5-10 mg per gram of food, beverage, medicine or dietary supplement.

EXAMPLES

In small scale operations, sonication is applied with an ultrasonic device such as Hielscher model UP50H with the following specifications: Power—50 Watts, Amplitude—30 kHz (Amplitude adjustable 20%-100%; Pulse adjustable to 0%-100%). In large scale operations, an ultrasonic flow-through reactor may be used, such as the UPR Flow-through Reactor model (2 kW, 40 Hz, 13 Gal/min) from the Ultrasonic Power Corp. (Freeport, Ill.). Rebaudioside A content and steviol glycosides were measured by HPLC (HPLC model Waters e2695, Detector: Waters 2489, specific detection threshold for the HPLC UV detector is 0.0001 AU (equal 0.1 mAU)). The 2489 UV/Vis detector easily integrates trace impurities down to 0.006% and lower.

Example 1

Stevia extracts with total glycosides content of 80%-95%, rebaudioside A content of 30% to 50% and moisture of 5%-7% were obtained from a commercial source. 1 kilogram of this Stevia extract was dried in an oven overnight to obtain a final moisture content of 1%. Table 1 shows the steviol glycoside contents of the Stevia extracts in the various runs.

TABLE 1

Steviol glycoside contents of the *Stevia* extracts

| Runs | RA % (AUC) | SS % (AUC) | RF % (AUC) | RC % (AUC) | Dulcoside % (AUC) | Rubusoside % (AUC) | RB % (AUC) | Steviolbioside % (AUC) |
|---|---|---|---|---|---|---|---|---|
| 1 | 44.35 | 41.65 | 1.33 | 7.37 | 1.34 | 1.27 | | |
| 2 | 44.42 | 41.69 | 1.30 | 7.38 | 1.33 | 1.24 | | |
| 3 | 44.26 | 41.55 | 1.31 | 7.34 | 1.34 | 1.25 | 0.34 | |
| 4 | 43.97 | 41.28 | 1.33 | 7.23 | 1.32 | 1.90 | 0.45 | 0.29 |

TABLE 1-continued

Steviol glycoside contents of the *Stevia* extracts

| Runs | RA % (AUC) | SS % (AUC) | RF % (AUC) | RC % (AUC) | Dulcoside % (AUC) | Rubusoside % (AUC) | RB % (AUC) | Steviolbioside % (AUC) |
|---|---|---|---|---|---|---|---|---|
| 5 | 43.79 | 41.34 | 1.35 | 7.28 | 1.34 | 1.90 | 0.44 | 0.30 |
| 6 | 43.89 | 41.22 | 1.34 | 7.30 | 1.34 | 1.97 | 0.41 | |
| 7 | 43.95 | 41.36 | 1.35 | 7.26 | 1.34 | 1.92 | 0.40 | 0.25 |
| 8 | 43.95 | 41.36 | 1.35 | 7.26 | 1.34 | 1.92 | 0.40 | 0.25 |
| 9 | 43.97 | 41.28 | 1.33 | 7.23 | 1.32 | 1.90 | 0.45 | 0.29 |

470 grams of the dried Stevia extract was mixed with 2 liters of 99.5% (v/v) ethanol (preferably anhydrous) at room temperature of 25° C. This mixture was stirred until all the dried Stevia extract is dissolved. The solution was heated to reflux temperature of 78° C. over a period of 30 minutes and the temperature was maintained at 78° C. for 30 minutes. At this stage, the solution was sonicated for a period of time to initiate nucleation (see Table 2).

The solution was cooled to 5° C. over a period of 6 hours and retained at this temperature for 15 hours to allow crystals to develop and mature. The crystals were then separated from the solution, with a filter paper. Absolute ethanol was used to wash away any mother liquor within the pores of the filter cake on the filter paper. The amount of ethanol used for washing is approximately 250 ml. The reaction conditions are set forth in Table 2 below.

TABLE 2

Process Reaction Conditions

| Runs | Heating time (hr) | Reflux T (° C.) | Reflux time, (hr) | Cooling T, ° C. | Cooling time, (hr) | sonication time (min) | T at sonication ° C. |
|---|---|---|---|---|---|---|---|
| 1 | 0.5 | 78.5 | 0.5 | 6 | 6 | | |
| 2 | 0.5 | 78.5 | 0.5 | 6 | 6 | | |
| 3 | 0.5 | 78.5 | 0.5 | 6 | 6 | | |
| 4 | 0.5 | 78.5 | 0.5 | 6 | 6 | | |
| 5 | 0.5 | 78.5 | 0.5 | 6 | 6 | | |
| 6 | 0.5 | 78.5 | 0.5 | 6 | 6 | | |
| 7 | 0.5 | 78.5 | 0.5 | 6 | 6 | | |
| 8 | 0.5 | 78.5 | 0.5 | 6 | 6 | | |
| 9 | 0.5 | 78.5 | 0.5 | 6 | 6 | 30 mins | 25 (before heating) |

The filter cake is removed from the filter paper and weighed, and tests were done to establish loss on drying. Rebaudioside A content and steviol glycosides were measured by HPLC, and integration of peaks (area under the curve (AUC) with a detection level of 0.006%). Results are presented in Table 3

TABLE 3

Steviol glycoside content of the isolated cake

| Runs | Reb A % (AUC) | Stevioside % (AUC) | Reb F % (AUC) | Reb C % (AUC) | Dulcoside A % (AUC) | Rubusoside % (AUC) | Reb B % (AUC) | Reb A Yields |
|---|---|---|---|---|---|---|---|---|
| 1 | 65.32 | 25.38 | 1.30 | 6.46 | 0.48 | 0.41 | | 99.31% |
| 2 | 76.57 | 15.96 | 1.15 | 5.97 | 0.19 | | | 81.20% |
| 3 | 75.77 | 16.50 | 1.17 | 6.00 | 0.22 | 0.15 | | 80.92% |
| 4 | 75.29 | 16.26 | 1.18 | 5.87 | 0.25 | 0.36 | 0.33 | 83.34% |
| 5 | 76.09 | 15.69 | 1.17 | 5.87 | 0.21 | 0.31 | 0.26 | 89.53% |
| 6 | 75.21 | 16.44 | 1.20 | 5.96 | 0.24 | 0.34 | 0.25 | 84.61% |
| 7 | 76.18 | 15.59 | 1.20 | 5.96 | 0.22 | 0.30 | 0.20 | 81.60% |
| 8 | 76.36 | 15.60 | 1.17 | 5.83 | 0.21 | 0.29 | 0.21 | 83.02% |
| 9 | 80.00 | 13.10 | 1.70 | 5.20 | | | | 90% |

Steviolbioside not detected in any of the samples 1-9.

Example 2

320 grams of the filter cake is mixed in 2 liters of aqueous ethanol 88% v/v. The mixture is stirred until all the filter cake is dissolved. This solution is then heated to reflux temperature in 30 minutes and refluxed for another 30 minutes. Sonication is applied for 30 minutes during the refluxing period. Then, the solution is cooled to 8° C. in 12 hours to develop and mature crystals. The conditions are set forth in Table 4.

TABLE 4

Process Reaction Conditions

| Runs | Reflux temp (° C.) | Reflux time (hr) | Cooling to temp (° C.) | Seeding amount % DS | Seeding condition | sonication time (min) | Temp at sonication (° C.) |
|---|---|---|---|---|---|---|---|
| 1 | 60 | 0.5 | 15 | — | — | — | — |
| 3 | 60 | 0.5 | 25 | — | — | — | — |
| 3 | 60 | 0.5 | 8 | — | — | — | — |
| 4 | 40 | 0.5 | 20 | — | — | 30 | 40 during refluxing |
| 5 | 77 | 0.5 | 8 | — | — | — | — |
| 6 | 40 | 0.5 | 20 | 1% | Fill seed at finish refluxing at 40 C. | — | — |
| 7 | 77 | 0.5 | 8 | — | — | — | — |
| 8 | 40 | 0.5 | 20 | — | — | — | — |
| 9 | 40 | 0.5 | 20 | — | — | 30 | 40 during refluxing |

The crystals are separated with a filter paper and washed with 150 mL of absolute ethanol. The crystals are then dried. Steviol glycoside contents are presented in Table 5.

TABLE 5

Steviol Glycoside Content

| Runs | Reb A % (AUC) | Stevioside % (AUC) | Reb F % (AUC) | Reb C % (AUC) | Reb A yield |
|---|---|---|---|---|---|
| 1 | 99.80 | | 0.20 | | 60.46% |
| 3 | 99.89 | | 0.11 | | 61.65% |
| 3 | 99.83 | | 0.18 | | 69.25% |
| 4 | 99.77 | | 0.23 | | 70.32% |
| 5 | 98.30 | 0.80 | 0.54 | 0.36 | 70.24% |
| 6 | 99.74 | 0.26 | | | 60.71% |
| 7 | 98.68 | 0.55 | 0.47 | 0.31 | 70.04% |
| 8 | 99.61 | | 0.28 | 0.11 | 63.50% |
| 9 | 99.90 | | 0.10 | | 72.43% |

Dulcoside A, Rubusoside, Reb B and Steviolbioside are not detected in any of the samples 1-9.

Example 3

Stevia Extract having a total steviol glycosides content of 80-95%, rebaudioside A content of 30% to 50%, moisture of 5%-7% was dried to moisture of less than 1%. The dried Stevia extract was mixed with absolute, non-denatured ethanol 99.5% or anhydrous ethanol in the ratio of 1 kg of stevia extract with 3.5 liters of ethanol. The solution of Stevia extract was heated from room temperature to reflux at atmospheric pressure over 30 minutes and maintained at reflux for 30 minutes. Sonication was applied with an amplitude of 45 kHz on a continuous basis for about 15 to 30 minutes to initiate nucleation. The solution was then cooled to 5° C. over 6 hours and maintained at 5° C. for 15 hours for crystals to mature. The crystals were separated from the mother liquor with a centrifuge. The crystals may be washed at this time with absolute ethanol to improve the purity of the crystals. The mother liquor was filtered. Ethanol from the mother liquor may be recycled via evaporation. The ethanol is recovered and dehydrated to be reused in the process.

The crystals were mixed with aqueous non-denatured ethanol 88% in the ratio of 1 kg of crystals with 6.25 liters of aqueous ethanol 88%. The solution was heated from room temperature to reflux at atmospheric pressure over 30 minutes and retain at reflux for 30 minutes. The solution was cooled to 8° C. over 12 hours. Sonication was applied at an amplitude of 45 kHz on a continuous basis for about 15 to 30 minutes to initiate nucleation. The solution was then maintained at 8° C. for 9 hours to allow the matured crystals to develop. The crystals are separated from the mother liquor with a centrifuge. The crystals were then washed with absolute ethanol at a ratio of 1 kg of crystals with a 5 kg of ethanol. The crystals were then dried at a temperature of 50° C. applying a vacuum of 25 mmHg. The mother liquor was filtered and ethanol was recycled from mother liquor via evaporation. The ethanol was dehydrated to be reused in the process. The solids isolated from the mother liquors may be recovered and reused as raw material in further purification processes such as described above to improve the total recovery of rebaudioside A, or isolate any of the other steviol glycosides.

Example 4

Production of purified rebaudioside A can be conducted in scale operations, such as in a pilot or industrial production batch. In large scale operation it is preferred to use a flow-through ultrasonic vessel such as the UPR Flow-through Reactor model (2 kW, 40 Hz, 13 Gal/min) from the Ultrasonic Power Corp. (Freeport, Ill.) (shown in FIG. 5). A series of vessels are provided such as according to FIGS. 6-8, that comprise at least a reactor with a jacketed mantel connected to a heat exchanger, a circuits and pumps to move the solution or slurry from a vessel to another, an ultrasonic device, a filter, and optionally a distillation unit.

The Stevia extract or the crude rebaudioside A is placed in the reactor with the appropriate amount of solvent (in a similar ratio as identified in examples 2-3). The heated solution is passed through the ultrasonic vessel under conditions and flow rates as identified in Table 6. The solution is then transferred either into the same vessel, or a separate vessel to be cooled to the desired temperature, such as the ones identified in examples 2-3. Once the crystals have matured the slurry of crystals is transferred to a filtration vessel and the crystals are separated from the mother liquor. Optionally, the crystals are washed with additional dried solvent. The crude or purified rebaudioside A can then be dried for storage and used as a sweetener, or subjected as is to another round of crystallization.

TABLE 6

Parameters for use of a sonication vessel

| | Volume of the batch (liter) | Power (watts) | Frequency (kHz) | Sonication Period (seconds) | Total Energy transferred (KJ/liter) | Pumping rate (liter/s) |
|---|---|---|---|---|---|---|
| Lab Scale | 2 | 20 | 30 | 1800 | 18 | — |
| Pilot Plant | 50 | 1000 | 40 | 900 | 18 | 0.056 |
| Commercial Plant | 10000 | 50000 | 40 | 3600 | 18 | 2.78 |

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A process of purifying rebaudioside A comprising:
forming a supersaturated solution of a steviol glycoside mixture comprising rebaudioside A and ethanol, wherein the supersaturated solution comprises at least 160 g/L of the steviol glycosides;
cooling the supersaturated solution to 40° C.; and
exposing the supersaturated solution to sonication to induce nucleation of crystals containing the rebaudioside A.

2. The process of claim 1, wherein ethanol comprises about 20% water.

3. The process of claim 1, wherein ethanol comprises no more than about 0.5% water.

4. The process of claim 1, wherein ethanol is anhydrous.

5. The process of claim 1, wherein exposing the supersaturated solution to sonication is performed for a continuous period of at least about 15 mins.

6. The process of claim 1, wherein exposing the supersaturated solution to sonication is performed for a continuous period of about 30 mins.

7. The process of claim 1, wherein exposing the supersaturated solution to sonication is performed in a continuous flow sonication vessel.

8. The process of claim 1, wherein exposing the supersaturated solution to sonication is performed at a power of 50 Watts and a frequency of 30 kHz.

9. The method of claim 8, wherein forming the supersaturated solution of the steviol glycoside mixture comprising rebaudioside A and ethanol, wherein the ethanol comprises about 5 to 20% of water.

10. The process of claim 1, wherein the sonication is performed by continuous sonication.

11. The process of claim 1, further comprising isolating rebaudioside A having at least 65±1% of rebaudioside A, and no more than 25±1% of stevioside.

12. The process of claim 1, further comprising isolating rebaudioside A having at least 75±1% of rebaudioside A, and no more than 17±1% of stevioside.

13. The process of claim 1, further comprising isolating rebaudioside A having at least 80±1% of rebaudioside A, and no more than 14±1% of stevioside.

14. The method of claim 13, further comprising drying the steviol glycoside mixture so that its water content is no more than 1%.

15. The method of claim 13, further comprising drying the steviol glycoside mixture so that its water content is no more than 0.5%.

16. The method of claim 13, wherein forming the supersaturated solution of the steviol glycoside mixture comprising rebaudioside A and ethanol is performed by heating the supersaturated solution to reflux of the steviol glycoside mixture.

17. The method of claim 13, wherein cooling the supersaturated solution to 40° C. and exposing the supersaturated solution to sonication lasts for about 30 mins.

18. The method of claim 13, wherein the sonication is applied at a power of at least 30 Watts and an amplitude of at least 30 Hz.

19. The process of claim 13, wherein the isolated rebaudioside A has at least 99±1% of rebaudioside A.

20. The process of claim 13, wherein the isolated rebaudioside A has at least 99.5±1% of rebaudioside A.

21. The process of claim 13, wherein the isolated rebaudioside A has at least 99.8±1% of rebaudioside A.

22. The process of claim 13, wherein the isolated rebaudioside A has at least 99.9±1% of rebaudioside A.

23. The method of claim 13, wherein forming the supersaturated solution of the steviol glycoside mixture comprising rebaudioside A and ethanol is performed by heating the solution to reflux of the solvent mixture.

24. The method of claim 23, wherein forming the supersaturated solution of the steviol glycoside mixture comprising rebaudioside A and ethanol is performed with absolute ethanol with a water content is no more than 0.5%.

25. A process of purifying rebaudioside A comprising:
forming a supersaturated solution of a Steviol glycosides mixture comprising at least 65±1% of rebaudioside A, no more than 25±1% of stevioside and an impurity profile of no more 6.5±0.1% of rebaudioside C, 1.3±0.1% of rebaudioside F, and no more than 1.0±0.05% of remaining Steviol glycosides in a solvent mixture of absolute ethanol and water, wherein the supersaturated solution comprises at least 160 g/L of the Steviol glycosides; and
exposing the supersaturated solution to sonication to induce nucleation of crystals containing the rebaudioside A.

26. A method of purifying rebaudioside A comprising:
forming a supersaturated solution of a *Stevia* extract in a solvent mixture of absolute ethanol and no more than about 2% water, wherein the supersaturated solution comprises at least 160 g/L of the *Stevia* extract; and
sonicating the supersaturated solution to induce nucleation of crystals containing rebaudioside A.

27. A method of purifying rebaudioside A comprising:
forming a supersaturated solution of a *Stevia* extract in a first solvent mixture of absolute ethanol and water, wherein the supersaturated solution comprises at least 160 g/L of the *Stevia* extract;
exposing the supersaturated solution to sonication to induce nucleation of crystals containing the rebaudioside A;

isolating a first composition comprising rebaudioside A;
forming a supersaturated solution of the first composition in a second solvent mixture of absolute ethanol and water, wherein the supersaturated solution comprises at least 160 g/L of the first composition;
exposing the supersaturated solution of the first composition to sonication to induce nucleation of crystals containing the rebaudioside A; and
isolating a second composition comprising rebaudioside A having a purity of at least 98.7%.

28. A method of purifying rebaudioside A comprising:
forming a supersaturated solution of a *Stevia* extract in a anhydrous ethanol, wherein the supersaturated solution comprises at least 160 g/L of the *Stevia* extract;
isolating a first composition comprising rebaudioside A;
forming a supersaturated solution of the first composition in a solvent mixture of ethanol and water;
exposing the supersaturated solution of the first composition to sonication to induce nucleation of crystals containing the rebaudioside A; and
isolating a second composition comprising rebaudioside A, the second composition having a purity of at least 99.5%.

* * * * *